United States Patent [19]

Hayes

[11] Patent Number: 5,100,404
[45] Date of Patent: Mar. 31, 1992

[54] INTRAMEDULLARY NAILING METHOD AND APPARATUS

[75] Inventor: Wilson C. Hayes, Lincoln, Mass.

[73] Assignee: Beth Israel Hospital, Boston, Mass.

[21] Appl. No.: 577,366

[22] Filed: Sep. 4, 1990

[51] Int. Cl.⁵ .................... A61B 17/56; A61F 2/32
[52] U.S. Cl. ........................ 606/62; 606/64; 606/98
[58] Field of Search .......... 606/62, 61, 63, 65, 606/67, 87, 88, 96, 97, 99, 100, 102, 103, 104, 86, 59, 98

[56] References Cited

U.S. PATENT DOCUMENTS

| | | | |
|---|---|---|---|
| 3,439,671 | 4/1969 | Kuntscher | 128/832 |
| 4,423,721 | 1/1984 | Otte | 606/100 |
| 4,475,545 | 10/1984 | Edner | 128/92 |
| 4,519,100 | 5/1985 | Wills et al. | 3/1.9 |
| 4,522,202 | 6/1985 | Otte et al. | 128/92 |
| 4,531,517 | 7/1985 | Forte | 606/99 |
| 4,590,930 | 5/1986 | Kurth | 606/63 |
| 4,628,920 | 12/1986 | Mathis, Jr. et al. | 128/92 |
| 4,667,663 | 5/1987 | Miyata | 128/92 |
| 4,697,585 | 10/1987 | Williams | 606/64 |
| 4,705,027 | 11/1987 | Klaue | 606/64 |
| 4,733,654 | 3/1988 | Marino | 606/64 |
| 4,805,607 | 2/1989 | Englhardt et al. | 128/92 |
| 4,817,591 | 4/1989 | Klaue | 606/64 |
| 4,846,162 | 7/1989 | Moehring | 606/64 |
| 4,877,019 | 10/1989 | Vives | 128/92 |
| 4,881,535 | 11/1989 | Sohngen | 606/98 |
| 4,895,572 | 1/1990 | Chernoff | 623/23 |
| 4,903,692 | 2/1990 | Reese | 606/99 |
| 4,913,137 | 4/1990 | Azer | 606/65 |

FOREIGN PATENT DOCUMENTS

| | | |
|---|---|---|
| 2440045 | 4/1975 | Fed. Rep. of Germany. |
| 2440045A1 | 4/1975 | Fed. Rep. of Germany. |
| 1034730A | 8/1983 | U.S.S.R. . |
| 8906948 | 8/1989 | World Int. Prop. O. ............ 606/64 |

Primary Examiner—Robert A. Hafer
Assistant Examiner—Michael Brown
Attorney, Agent, or Firm—Bromberg & Sunstein

[57] ABSTRACT

The present invention provides a method and apparatus for achieving the fixation of a bone having a medullary canal, and in particular permits the secure and highly repeatable location of the distal locking screws used in intramdedullary nailing of long bone fractures. In accordance with a preferred embodiment of a method of the invention the distal end of an intramedullary nail is locked to the distal portion of a bone by inserting a guide wire into the medullary canal of the bone, drilling a pilot hole through the near cortex of the bone, and using a suitable locator tool that has an arrangement for grabbing the guide wire. The locator tool also has an arrangement for engaging with a suitably configured intramedullary nail. The intramedullary nail is then inserted until it engages with the locator. A distal alignment fixture engaged with the locator can then be used to determine the location of the first distal locking hole. After insertion of the first distal locking screw, the second distal locking screw can be located. The invention also provides apparatus for achieving the foregoing, as well as methods and apparatus for adjusting the compression of distal and proximal bone fragments and placement of the proximal locking screw or screws.

16 Claims, 13 Drawing Sheets

INTRAMEDULLARY NAILING METHOD AND APPARATUS

TECHNICAL FIELD

The present invention relates to methods and apparatus for achieving the fixation of long bone fractures utilizing intramedullary nails.

BACKGROUND ART

One approach to the internal fixation of long bone fractures is to insert a relatively flexible intramedullary nail into the medullary canal so that it crosses the fracture site and provides increased rigidity to the fracture fragments. Until recently, such devices have been viewed as gliding splints, allowing the fracture fragments to collapse slightly as weightbearing loads are applied and fracture healing proceeds. Under these conditions, fixation rigidity depends on close-fitting frictional load transmission between intramedullary nail and bone and on adequate contact between the proximal and distal fracture fragments. As a result, intramedullary nails have not traditionally been used with fractures near the bone ends or with severely comminuted central shaft fractures where bone collapse and marked shortening could occur.

In attempts to expand the indications for intramedullary nailing to these fracture types, a number of manufacturers have developed "locking" systems, which are designed to provide secure attachment between the intramedullary nail and the most proximal and distal fracture fragments. Such locking systems prevent collapse of severely comminuted fractures, allow weightbearing relatively early, and increase the torsional, flexural and axial rigidity and strength of the bone-implant system. The availability of these locking systems has resulted in a dramatic increase in the use of intramedullary nailing, to the point that it is the treatment of choice for most long bone fractures of the lower extremity.

Several approaches are used to provide proximal and distal locking of intramedullary nails. These include the use of expanding bolts (U.S. Pat. No. 4,590,930 for an invention of Kurth et al.), fins (West German patent application laid open as number 24 40 045 on Apr. 10, 1975; U.S. Pat. No. 4,519,100 for an invention of Wills et al.), and multiple protruding pins, all operated by screw-type insertions along the length of the nail. (See also the discussion in column 1 of U.S. Pat. No. 4,733,654 for an invention of Marino and columns 1-2 of U.S. Pat. No. 4,697,585 for an invention of Williams.) By far the most popular approach, however, is to employ transverse screws or bolts, which are inserted through transverse holes in the intramedullary nail and corresponding holes drilled in the bone cortices. Such locking screws can be perpendicular or oblique to the longitudinal axis of the bone and can be used singly or in pairs to provide a rigid connection between nail and bone fragment.

In the process of intramedullary nailing, it is common to insert initially, into the medullary canal from the proximal end thereof, a ball-ended guide wire and then to pass this guide wire down the canal to locate the distal fracture fragment. Thereafter a series of flexible intramedullary reamers are passed in succession over the guide wire. The guide wires are also intended to allow withdrawal of the reamer tip in the unlikely case that the reamer breaks during the reaming process. Once reaming is completed, the ball-ended guide wire is usually replaced with a smooth-tipped guide wire and the hollow intramedullary nail is inserted over the guide wire. Once successful positioning of the intramedullary nail is achieved, the guide wire is withdrawn and proximal and distal locking screws are inserted. See U.S. Pat. No. 4,913,137, for an invention of Azer et al.

The prior art has frequently attempted to address the problem of positioning holes, drilled in the most proximal and distal bone fragments, in proper relation to the corresponding holes in the intramedullary nail, so that the locking screws can be inserted to fix the position of the nail vis-a-vis these bone fragments. For proximal locking, it is straightforward to design fixtures that can be used intraoperatively as drill guides for locating the position of the proximal screw or screws. Typically, such devices attach temporarily to the proximal end of the nail, allow the transverse holes to be drilled through a special guide, and are then removed after screw insertion. See U.S. Pat. No. 4,733,654 for an invention of Marino. However, such an approach (described in U.S. Pat. Nos. 4,881,535 for an invention of Sohngen and 4,913,137 for an invention of Azer et al.), has proven unworkable with the distal transverse locking screws. Invariably some twisting and bending of the nail occurs during insertion and thus the geometric relationship between the proximal and distal ends of the nail cannot be determined with certainty.

As a consequence, there have been many attempts to develop locating devices for the distal locking screws that allow holes to be drilled through the bony cortices at the precise location of the distal holes in the intramedullary nail. Approaches have ranged from special radiographic targeting devices (much like bomb sights) to capture mechanisms which depend on prior insertion of the locking screw and a special configuration of the distal end of the nail. For the latter, see U.S. Pat. Nos. 4,817,591 and 4,705,027 for inventions of Klaue. The radiographic approaches are time-consuming, expose the surgeon to excess radiation and do not achieve proper location with absolute certainty. Capture mechanisms have proven unworkable, primarily because of nail deformation and an inability to hit the already inserted screw, and have thus never been marketed. Thus targeting and location of the distal locking screws remain the most time-consuming and problematic phase of the surgical procedure. While highly experienced surgeons eventually learn to accomplish this step successfully, it is considerably more difficult for inexperienced surgeons or for those who do not do intramedullary nailing with considerable frequency.

SUMMARY OF THE INVENTION

The present invention provides a method and apparatus for achieving the fixation of a bone having a medullary canal, and in particular permits the secure and highly repeatable location of the distal locking screws used in intramedullary nailing of long bone fractures. In accordance with a preferred embodiment of a method of the invention the distal end of an intramedullary nail is locked to the distal portion of a bone by inserting a guide wire into the medullary canal of the bone, drilling a pilot hole through the near cortex of the bone, and using a suitable locator tool that has an arrangement for grabbing the guide wire. The locator tool also has an arrangement for engaging with a suitably configured intramedullary nail. The intramedullary nail is then inserted until it engages with the locator. A distal alignment fixture engaged with the locator can then be used to determine the location of the first distal locking hole. After insertion of the first distal locking screw, the second distal locking screw can be located. The invention also provides apparatus for achieving the foregoing, as well as methods and apparatus for adjusting the compression of distal and proximal bone fragments and placement of the proximal locking screw or screws.

BRIEF DESCRIPTION OF THE DRAWINGS

The foregoing features of the present invention may be more readily understood by reference to the following detailed description taken with the accompanying drawings, in which.

DETAILED DESCRIPTION OF SPECIFIC EMBODIMENTS

Figure 1A:
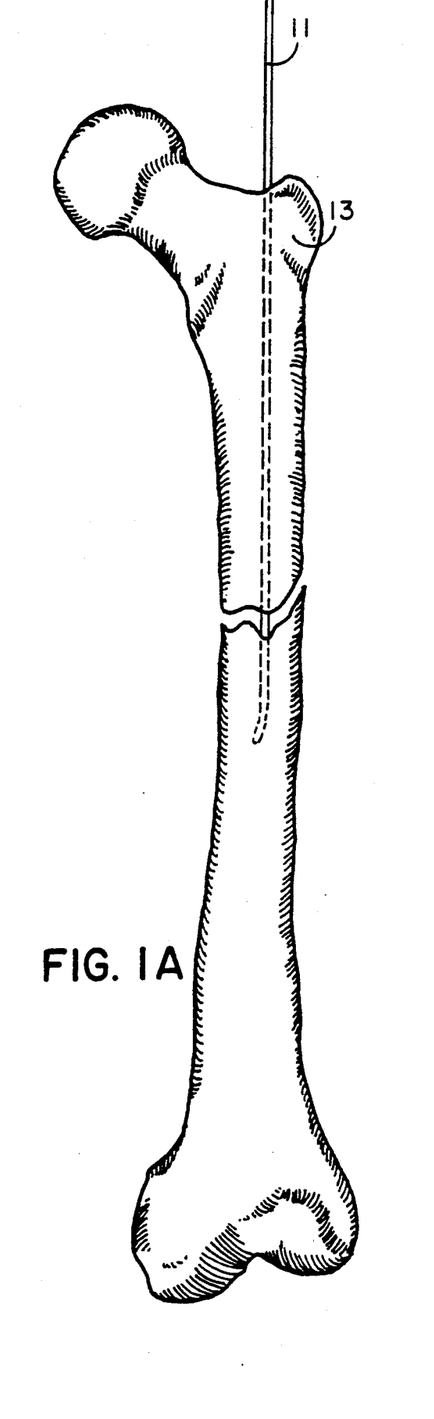
FIG. 1(A) presents an elevation of a bone and guide wire of the types to which the invention is applicable.
Figure 1B:
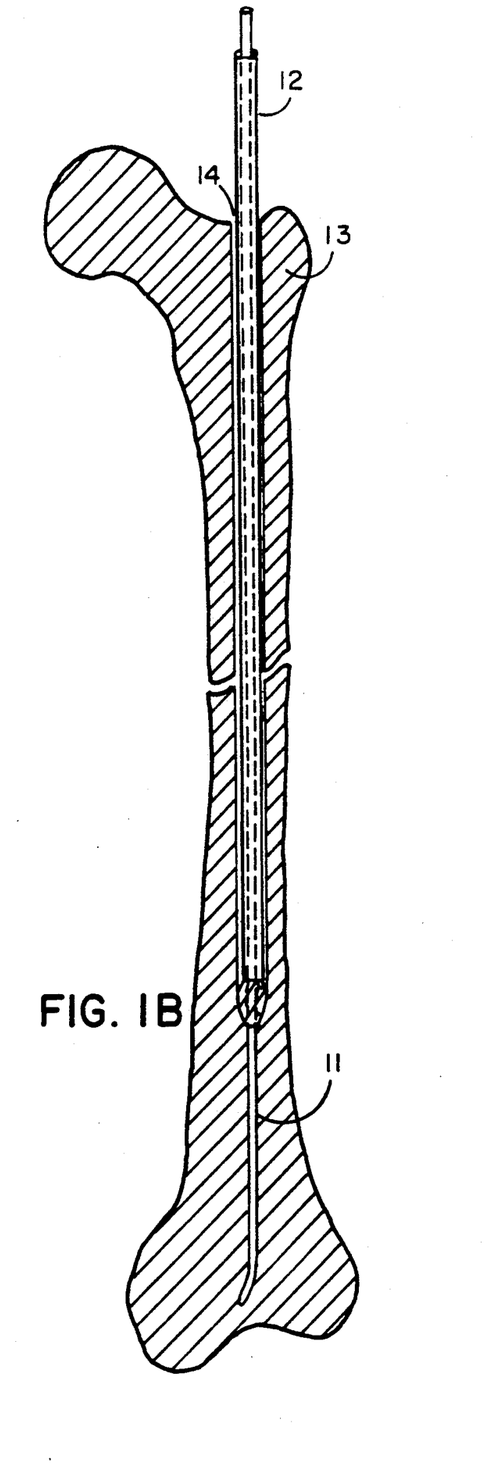
FIG. 1(B) illustrates in vertical section the use of an intramedullary nail with the guide wire of FIG. 1(A) in accordance with an embodiment of the invention.

In a preferred embodiment, the method and apparatus of the invention utilize the prior art guide wire that allows passage of the intramedullary nail. FIG. 1(A) illustrates such a guide wire 11, which, as described in the Background Art section above, is used after reaming of the medullary canal of a long bone such as femur 13. FIG. 1(B) shows an intramedullary nail 12, disposed concentrically around the guide wire 11, being guided through the canal 14.

Figure 2:
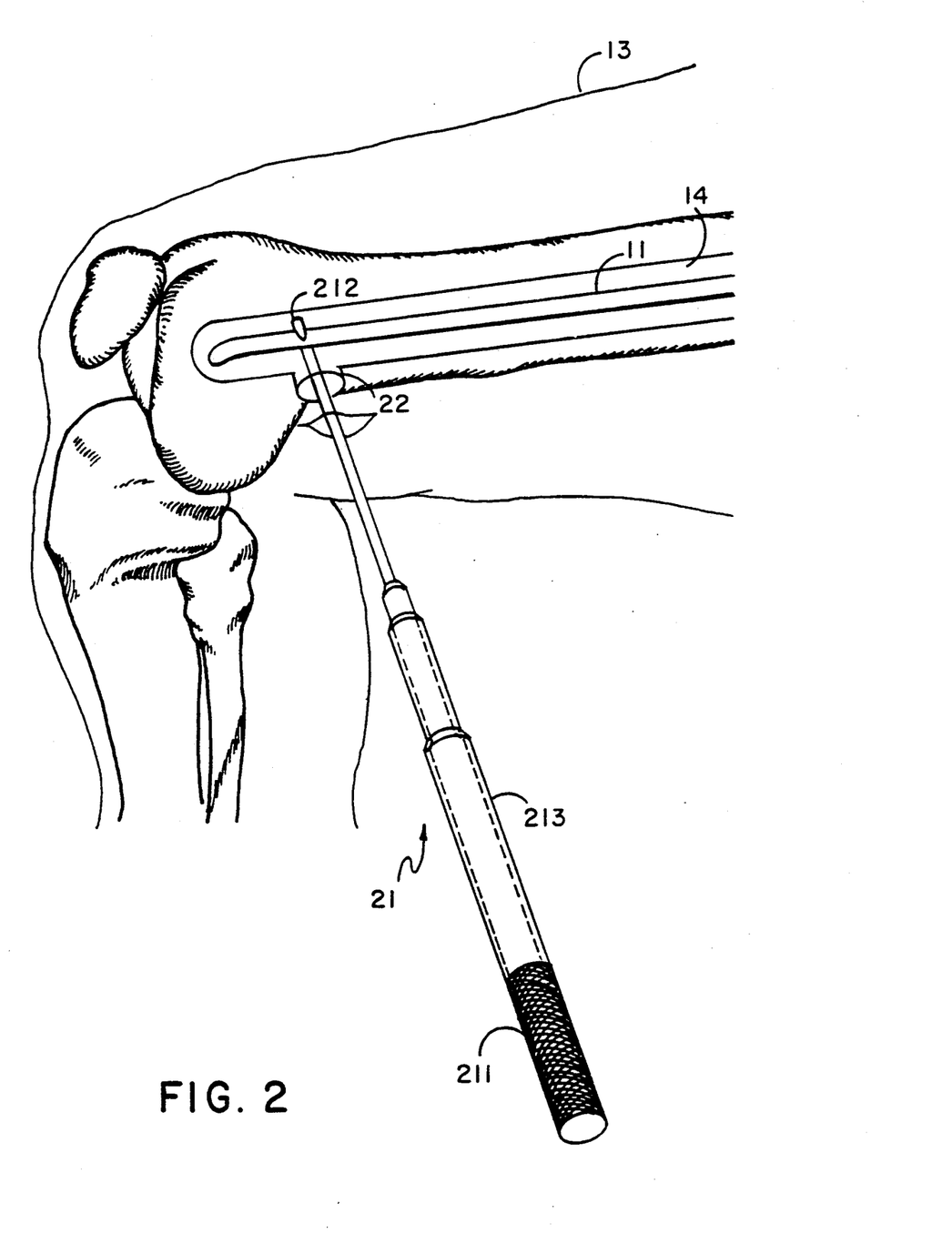
FIG. 2 shows in a cut away perspective view the use of a locator in accordance with a preferred embodiment of the invention grabbing the guide wire of FIG. 1.

In accordance with a preferred embodiment of the invention, before the intramedullary nail is positioned in the canal, there is drilled a pilot hole 22 in the near cortex of the bone through which is inserted the hook tip 212 of a locator 21. (As used in this description and in the following claims, the term to "drill" a hole refers to any method of forming a hole, regardless whether by means of a conventional drill or laser apparatus or otherwise.) The location of the pilot hole may be determined using anatomical markers and radiographic techniques. If desired the guide wire may be provided with a suitable radio-opaque marker for determination of longitudinal placement of the hole. The locator may be held by its handle 211 and is manipulated until the tip 212 grabs the guide wire 11. The locator has a sleeve 213 (which is initially held in the retracted position illustrated here) that is slidably mounted on the locator.

Figure 3:
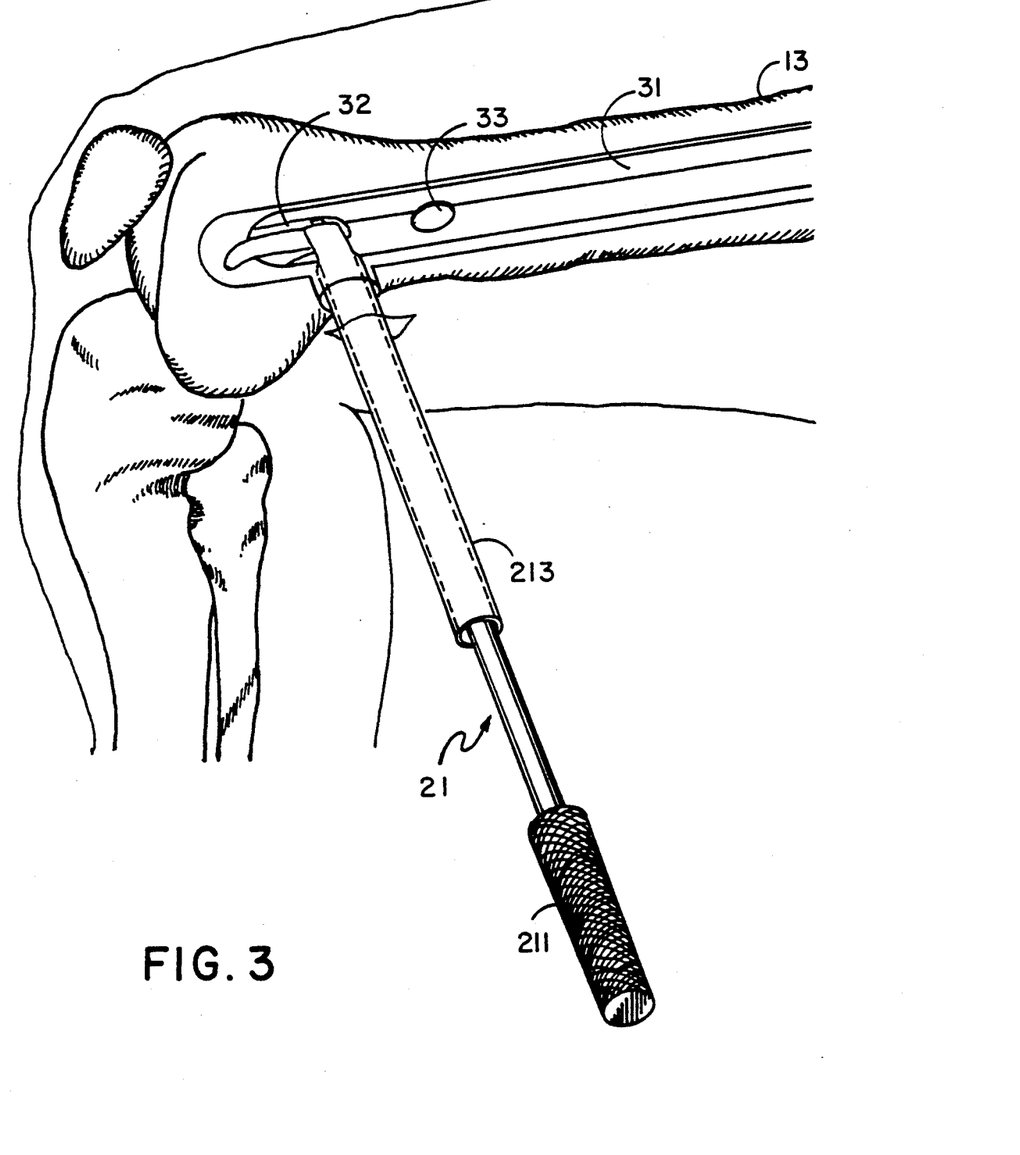
FIG. 3 shows the locator of FIG. 2 engaged with the distal end of an intramedullary nail in accordance with a preferred embodiment of the invention.

As shown in FIG. 3, after the guide wire 11 has been grabbed, the sleeve 213 is then moved to the extended position both to maintain the grasp of the hook on the guide wire and to present a feature that may be engaged with the distal end of the intramedullary nail 31. The locator 21 may be held with one hand while the nail is then inserted and manipulated until the engagement opening 32 at its distal end is engaged with the tip of sleeve 213 of the locator.

Figure 4:
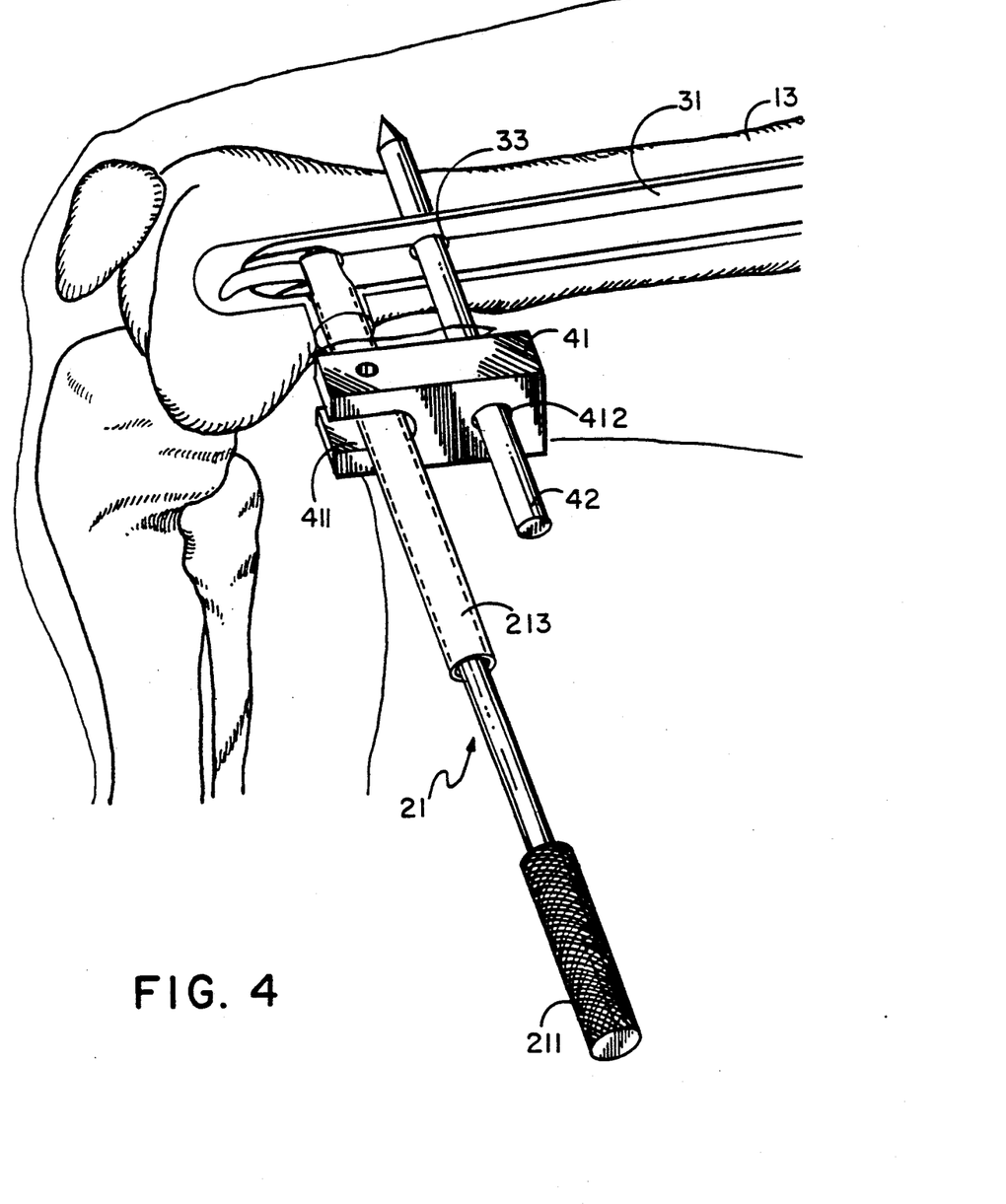
FIG. 4 shows a distal alignment fixture, in accordance with a preferred embodiment of the invention, engaged with the locator of FIG. 3.

The location for drilling in the bone a hole corresponding to the locking aperture 33 at the distal end of the nail 31 may then be determined in a manner illustrated in FIG. 4. As shown in FIG. 4, a distal alignment fixture 41 has an engagement region 411 that is engaged against the sleeve 213 of locator 21. The alignment hole 412 of the fixture 41 is used to guide drill 42 in drilling the hole, corresponding to locking aperture 33 of the nail, in the near and far cortices. To assure reliability in identifying a suitable location for the hole, the engagement region 411 may be keyed to sleeve 213 in the manner described below in connection with the distal alignment of FIGS. 14(A) and 14(B). Preferably, drilling of the hole is commenced before removal of the guide wire, so that the distal alignment fixture then has an orientation that is effectively fixed with respect to the guide wire.

Figure 5:
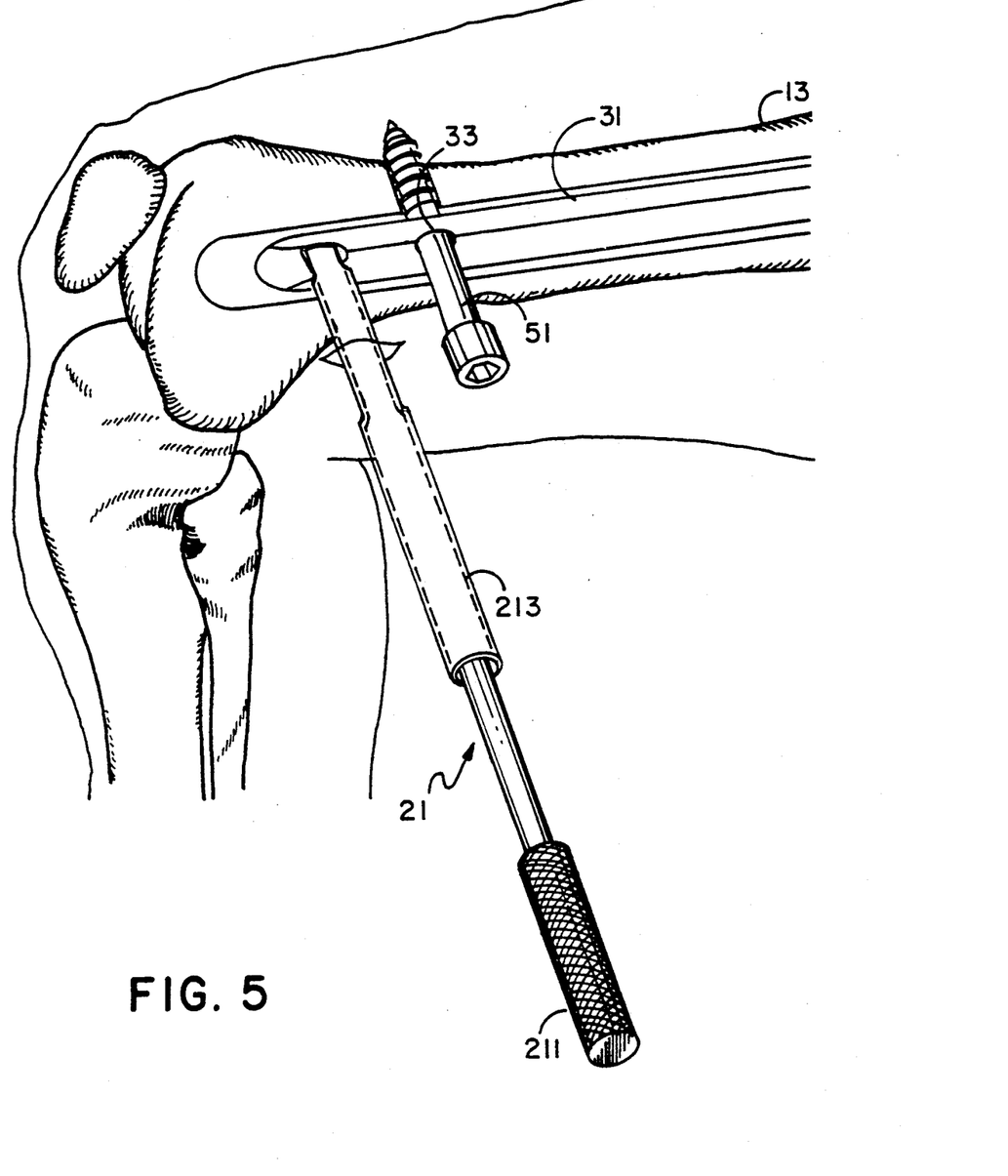
FIG. 5 shows placement of the first distal locking screw following use of the distal alignment fixture of FIG. 4.

As shown in FIG. 5, after the drilling has been completed, the fixture may be removed, and first locking screw 51 is inserted through the hole and through locking aperture 33, thus fixing the distal end of the nail 31 in relation to the distal bone fragment. The locator 21 may then be disengaged from the nail and removed from the pilot hole. Thereafter a second locking distal locking screw may be inserted using one of a variety of alternatives. In accordance with one embodiment, the same fixture 41 may be reversed and engaged with locking screw 51 (which initially is not screwed in quite completely) to provide alignment hole 412 as a guide for drilling to extend the pilot hole through the far cortex. (In such an instance the intramedullary nail 31 has a corresponding locking aperture—shown as item 139 in FIGS. 13(A) and 13(B)—situated beneath the pilot hole.) In accordance with another embodiment, however, a fixture (which may but need not be distinct from fixture 41) engaged with locking screw 51 may be used to determine the location of third distinct hole corresponding to the location of a separately located locking aperture in the nail 31; this aperture may be either distal or proximal of the aperture 33.

Figure 6:
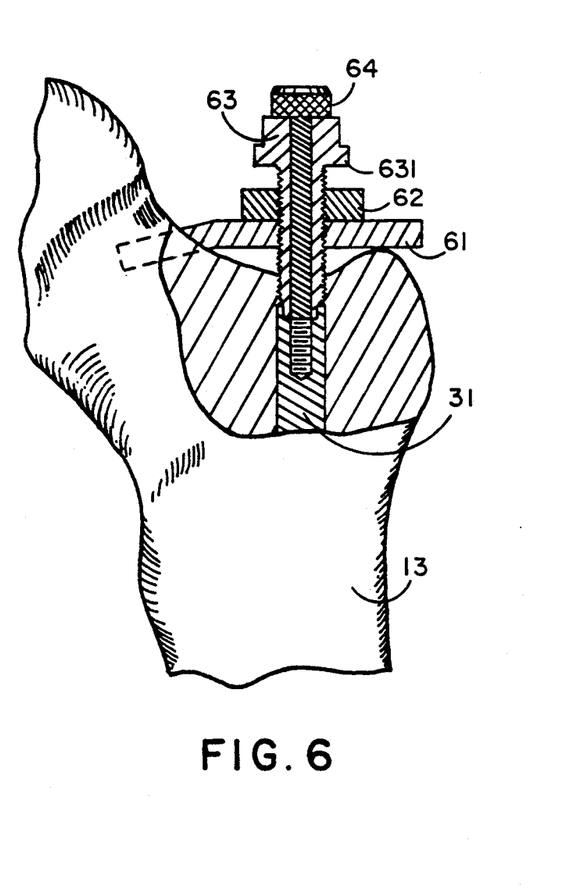
FIGS. 6 and 7 illustrate in a partial vertical section the use, in accordance with a preferred embodiment of the invention, of a compression nut and compression washer and bolt system at the proximal end of the intramedullary nail of FIG. 5 to achieve controlled compression of the bone fragments.
Figure 7:
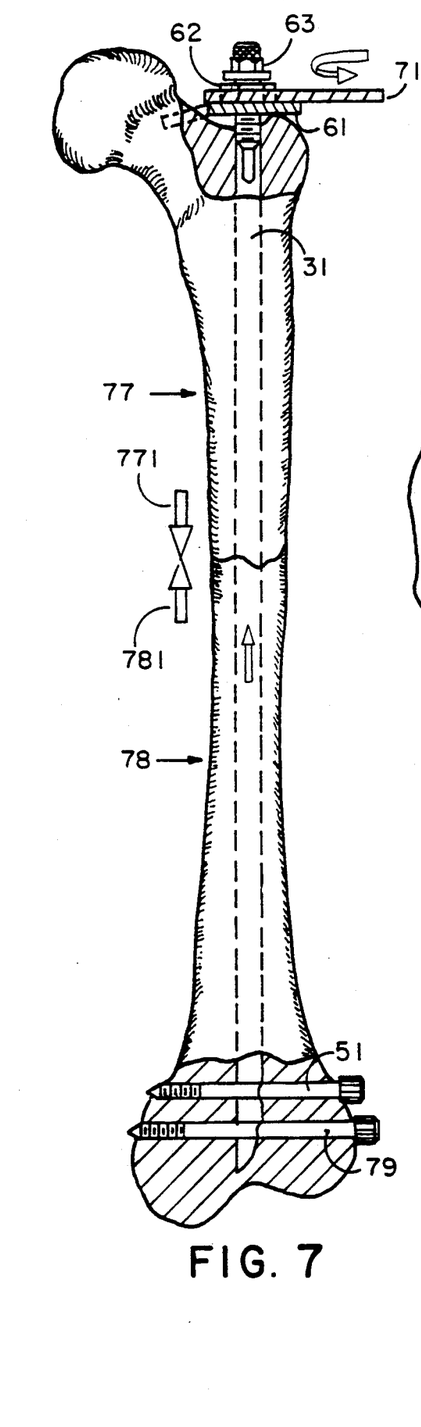

After placement of the distal locking screws, the proximal screw or screws may be inserted in a manner known in the art. Alternatively, as shown in FIG. 6, a concentric bolt system including inner and outer bolts 64 and 63 is employed. Outer bolt 63 includes a proximal flange 631 used to mount the alignment fixture in the manner discussed below. Inner bolt 64 is screwed into mating threads formed in the proximal end of the intramedullary nail 31. If controlled compression of the fracture fragments in relation to one another is desired, compression nut 62 and compression washer 61 are included on the outer bolt 63; then as shown in FIG. 7, the nut 62 is turned by wrench 71 so as to urge proximal fragment 77 in the relative downward direction 771 and distal fragment 78 in the upward direction 781 to a desired extent.

Figure 8:
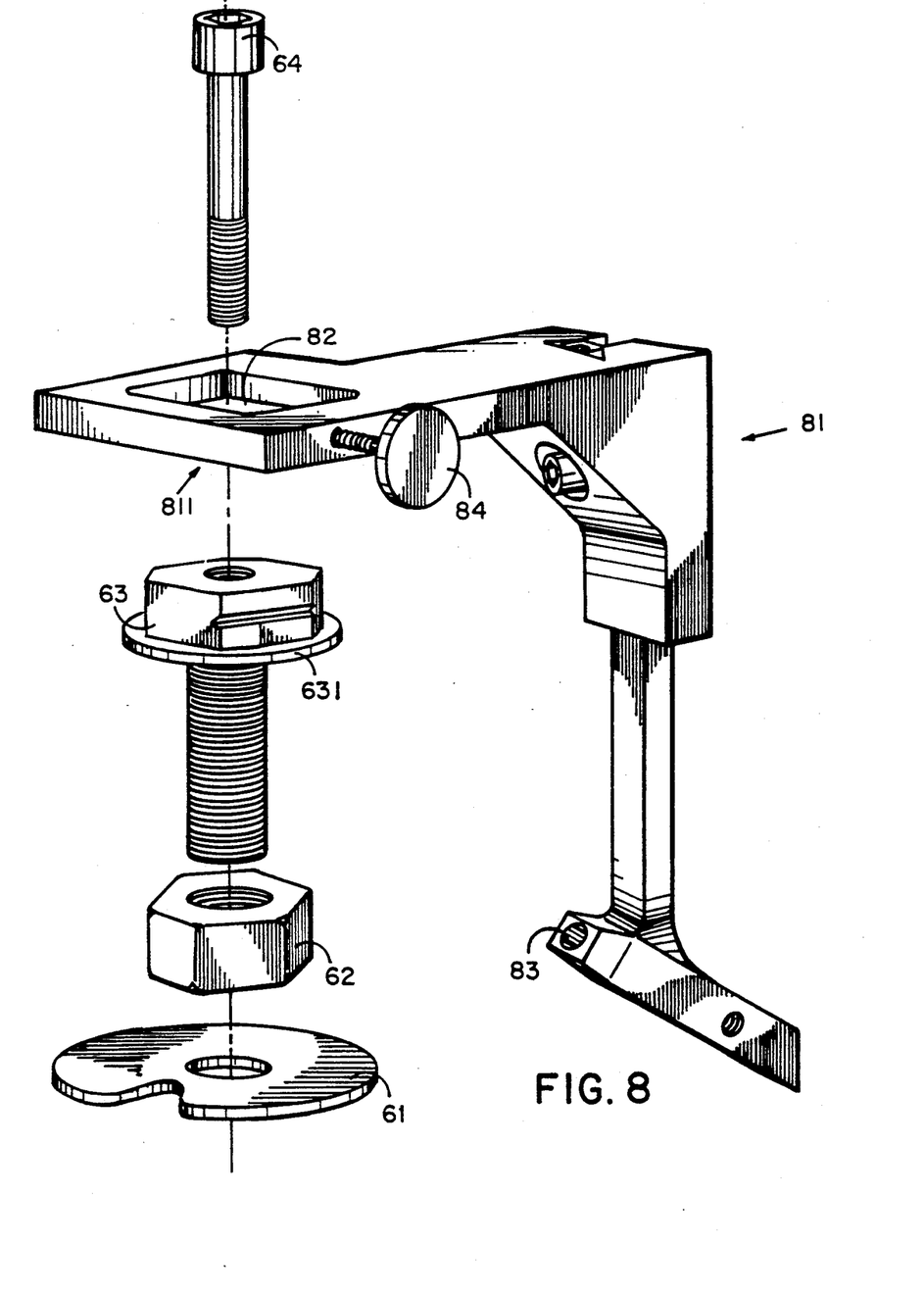
FIG. 8 is a perspective view of a proximal alignment fixture in accordance with a preferred embodiment of the invention.
Figure 9:
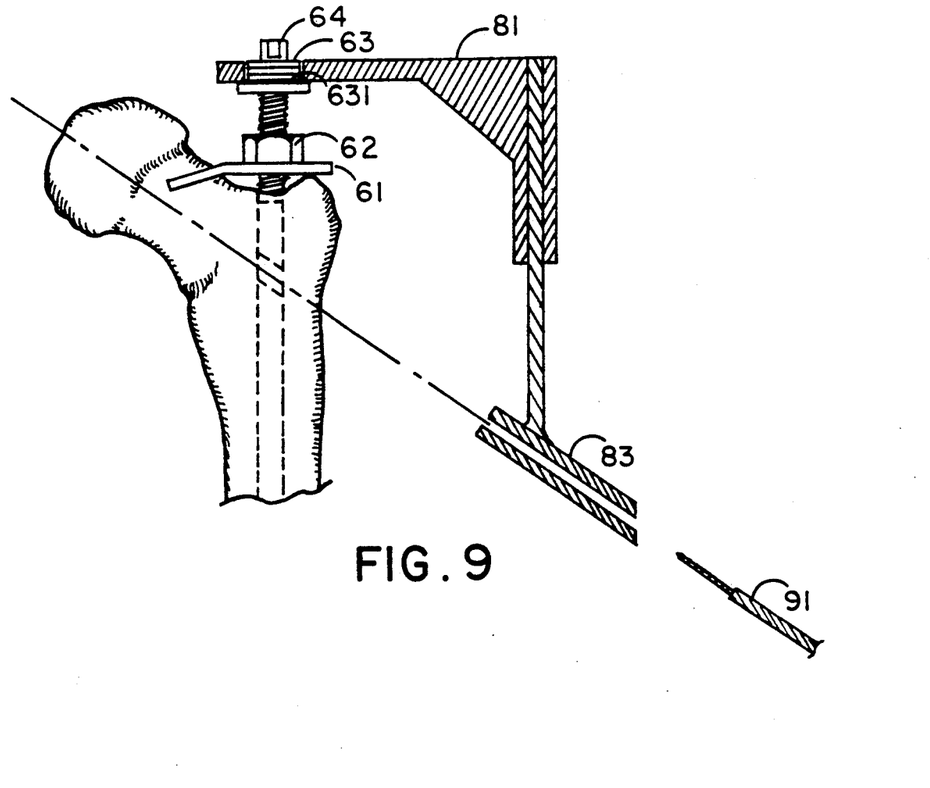
FIG. 9 shows use of the fixture in a partial vertical section.
Figure 10:
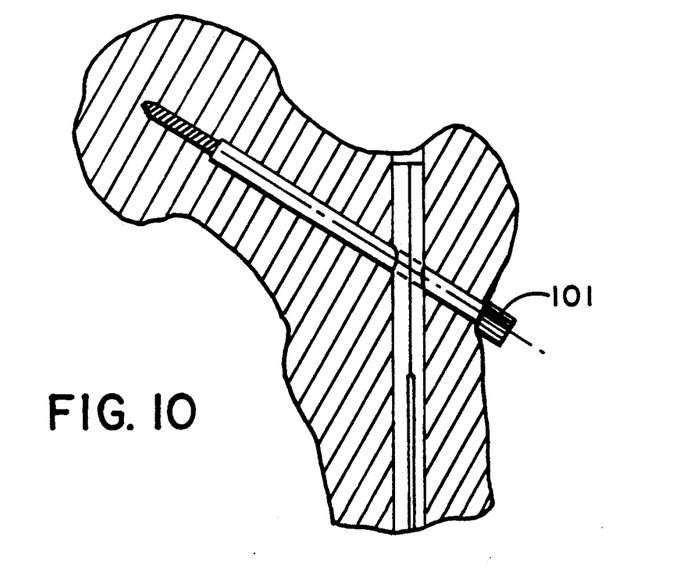
FIG. 10 is a vertical section illustrating placement of the proximal locking screw following use of the fixture.

Outer bolt 63 of FIG. 6 is also used to hold the proximal alignment fixture 81 in place. This fixture, shown in FIG. 8, has a drilling guide hole 83 and mounting aperture 82. As shown in FIG. 9, the fixture is positioned with the head of bolt 63 snugly disposed in the aperture 82, and the bottom surface 811 of the fixture 81 surrounding the aperture 82 rests on the flange 631 of the head of bolt 63 to hold the fixture in place. Set screw 64 locks the fixture to the head of bolt 63. The drilling guide 83 is used for guiding the drill 91 to drill the hole for the proximal locking screw 101, which is shown inserted in FIG. 10.

Figure 11:
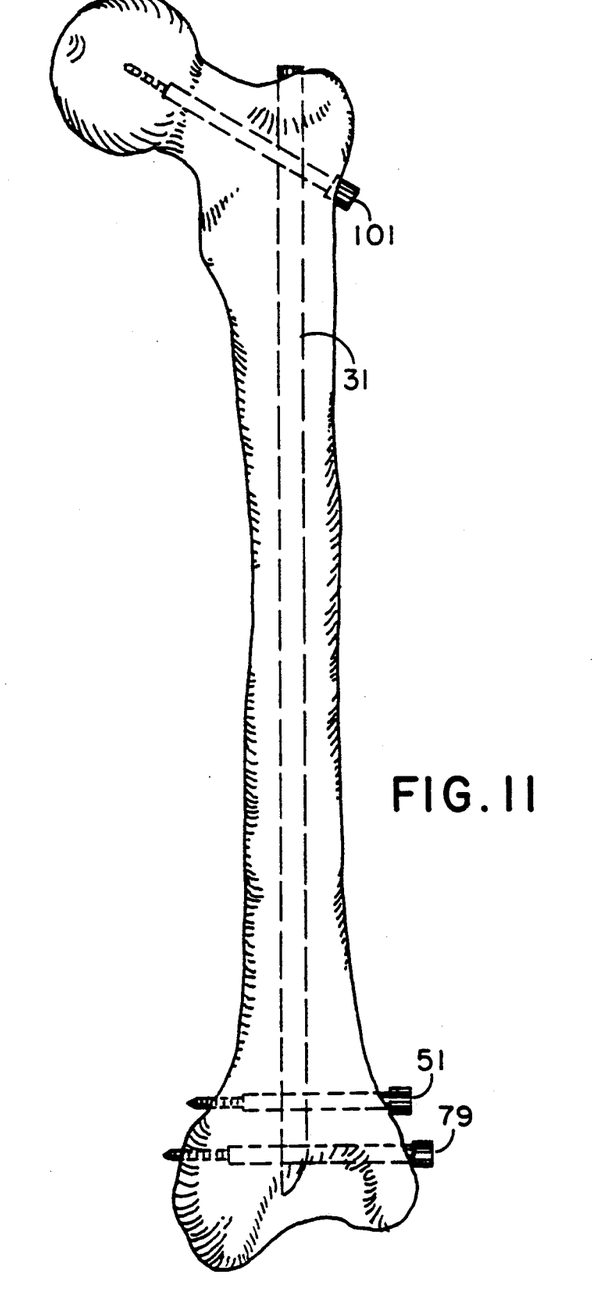
FIG. 11 is an elevation view of a femur experiencing fixation in accordance with the embodiments of the previous figures showing placement of the intramedullary nail and locking screws.

FIG. 11 shows the relative positions of the intramedullary nail 31, the proximal locking screw 101 and the distal locking screws 51 and 79 placed in accordance with the embodiments herein described.

Figure 12A:
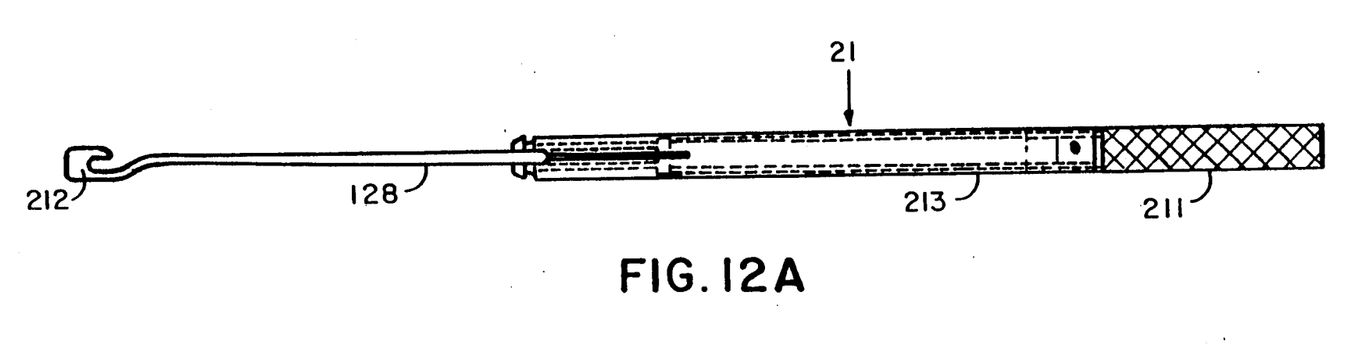
FIGS. 12(A) and 12(B) are elevation views of the locator of FIGS. 2-4 with sleeve retracted and extended respectively.
Figure 12B:
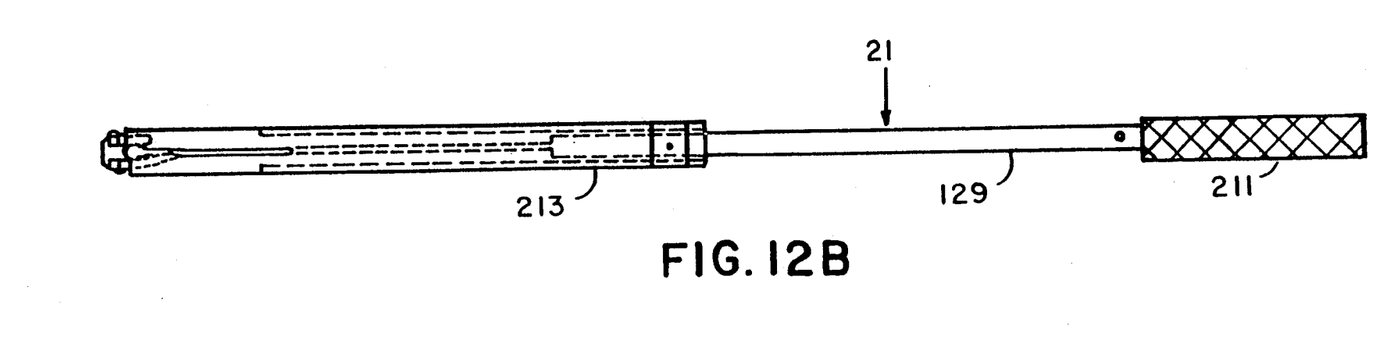

FIGS. 12(A) and 12(B) show the locator 21 in further detail with the sleeve 213 respectively retracted and extended along the longitudinal axis of the locator. The sleeve 213 is slidably mounted on the core 129. The hook tip 212 is formed on the rod 128 that is affixed to the core 129.

Figure 12C:
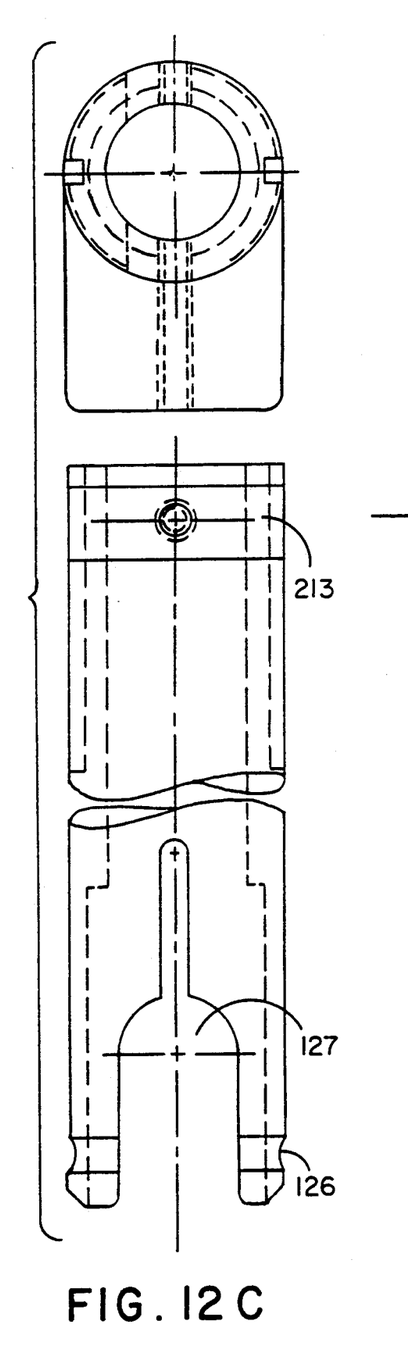
FIGS. 12(C) and 12(D) are front and side elevations showing detail of the sleeve.
Figure 12D:
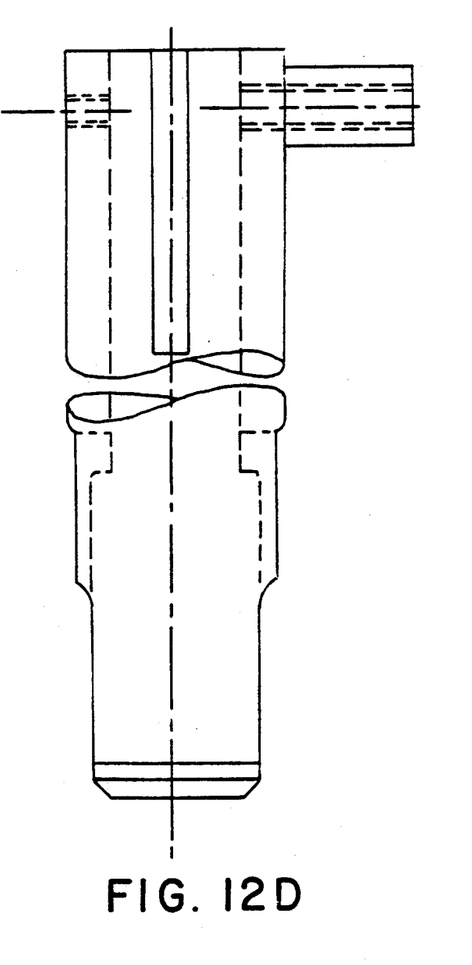

FIGS. 12(C) and 12(D) show the sleeve 213 in further detail. At the distal end of the sleeve are formed a U-shaped receiving region 127 for receiving the hooked tip 212 when the sleeve is extended and annular recess 126 for engagement in the engagement opening 32 at the distal end of the intramedullary nail 31.

The distal end of the intramedullary nail 31 is shown in FIGS. 13(A) through 13(D). In addition to first distal locking aperture 33, a second distal locking aperture 139 is provided. This aperture is formed only in the rear half of the wall forming the nail, since the front half is in this region absent on account of the presence of engagement opening 32.

Figure 13A:
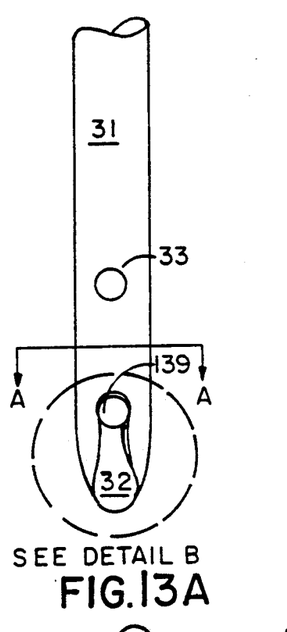
FIG. 13(A) is a front elevation of the distal end of the intramedullary nail of the previous figures.
Figure 13B:
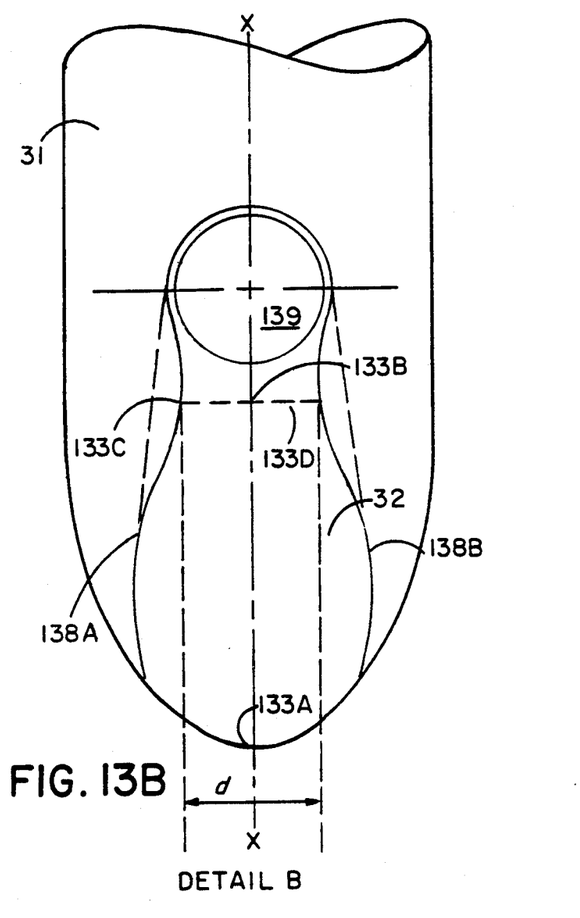
FIG. 13(B) shows in detail the engagement opening of the nail of FIG. 13(A)
Figure 13C:
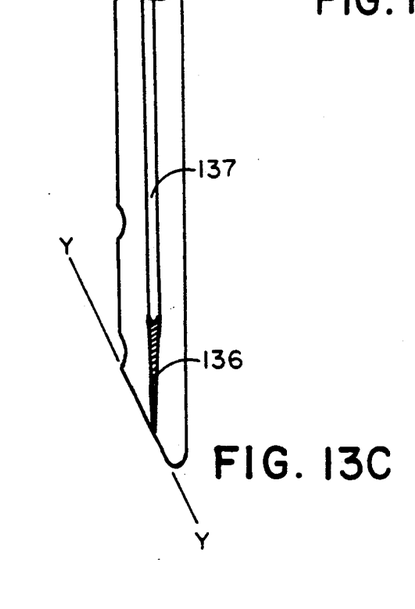
FIG. 13(C) is a side elevation of the nail of FIG. 13(A)

The shape of the engagement opening 32 is illustrated in detail in FIG. 13(B) from the front and in FIG. 13(C) from the side. As can be seen in FIG. 13(C) the end of the wall of the intermedullar nail generally defines an opening in the front of the member lying generally in the plane Y—Y. The effect of this geometry is shown in FIG. 13(B), in which it can be seen that the tip of the locator sleeve 213 in FIGS. 12A and 12B may be inserted into the opening with the sleeve disposed perpendicularly to the longitudinal axis X—X of the interior channel of the nail. The end of the wall is shaped so as to facilitate positioning of the nail and to cause its rotation to the extent necessary, on encountering the locator in an approximately correct position, to become positively engaged in the opening.

Figure 13D:
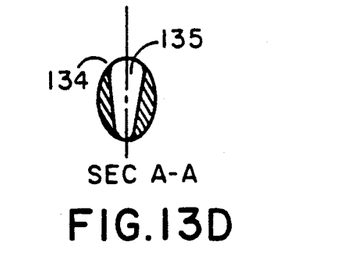
FIG. 13(D) is a cross section through the plane A—A of the nail of FIG. 13(A)

The shape of the end of the wall of the nail has bilateral symmetry with respect to the plane perpendicular to the page passing through the longitudinal axis. The shape can be analyzed in terms of the axial position of a projection of a location on the end of the wall onto the longitudinal axis as a function of the angular orientation of the location about the longitudinal axis. The most distal axial position 133a is associated with an angular orientation at the rear of the nail. As the angular orientation of a location on the end of the wall moves toward the front on regions 138a and 138b, the axial position associated with such location becomes smoothly and progressively less distal until axial position 133b associated with symmetrical points 133c and 133d on the end of the wall. Here the distance between the points 133c and 133d is approximately equal to the diameter of the sleeve 213 at its recess 126 shown in FIG. 12(C), and the wall is here on each side approximately parallel to the longitudinal axis. In the angular orientations lying predominantly between the points 133c and 133d, the wall defines a region into which the locator may be positively engaged by gripping in the recess 126 of sleeve 213 of FIG. 12A. This region lies in front of the locking aperture 139. The maximum spacing between opposing points on the wall increases slightly in this region beyond the spacing between points 133c and 133d in order to provide kinesthetic indication that the locator has been properly engaged in the nail. Also as shown in FIG. 13(C), the slot 137 along the side of the nail is closed in the most distal region 136 of the nail, for example, by soldering or welding. In order to facilitate centering of the guide wire 11 within the channel of the nail 31 (and therefore grabbing of the guide wire 11 by the locator 21), the cross section of the nail in the region marked by plane A—A in FIG. 13(A) is narrowed somewhat, for example, by silver soldering. The cross section is shown in FIG. 13(D) as item 135 and the narrowed cross section is item 134. The cross section must not be narrowed, however, so much that the tip of the guide wire cannot readily be removed from the channel within the nail.

Figure 14A:
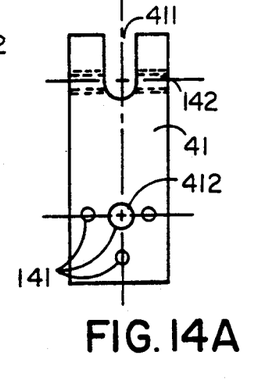
FIGS. 14(A) and (B) are bottom and side elevations respectively of the distal alignment fixture of FIG. 4.
Figure 14B:
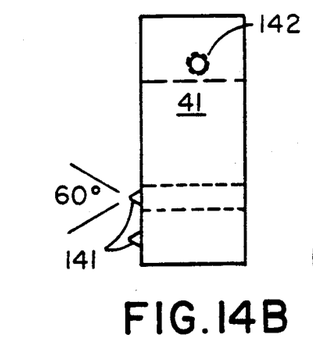

FIGS. 14(A) and 14(B) show detail of the distal alignment fixture 41 (see FIG. 4), which is provided with teeth 141 on the underside for facilitating stabilization of the fixture. Although the sleeve 213 has been shown as cylindrical in shape, it may have one or more flat sides that are keyed to the engagement region 411 of the fixture 41 for further stabilization.

Figure 15A:
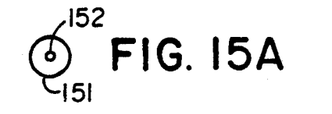
FIGS. 15(A), (B), and (C) illustrate inserts used in connection with the distal alignment fixture of FIG. 14.
Figure 15B:
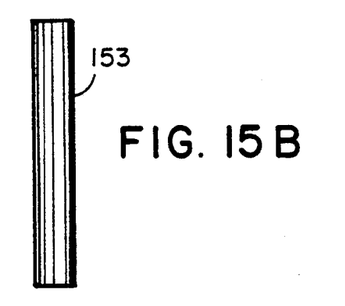
Figure 15C:
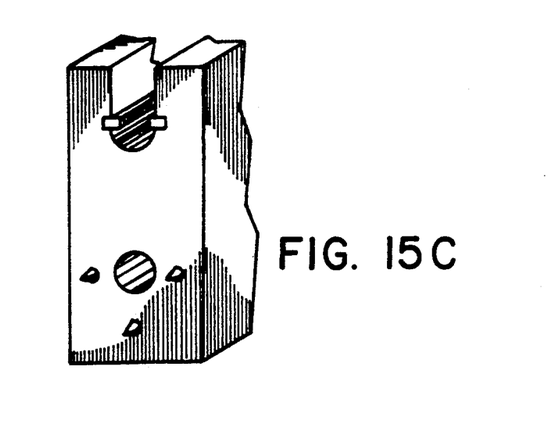

FIGS. 15(A) and 15(B) illustrate inserts used with the fixture 41, including a bushing 151 for a K-wire inserted through channel 152, which fits concentrically within drill guide 153.

Figure 16:
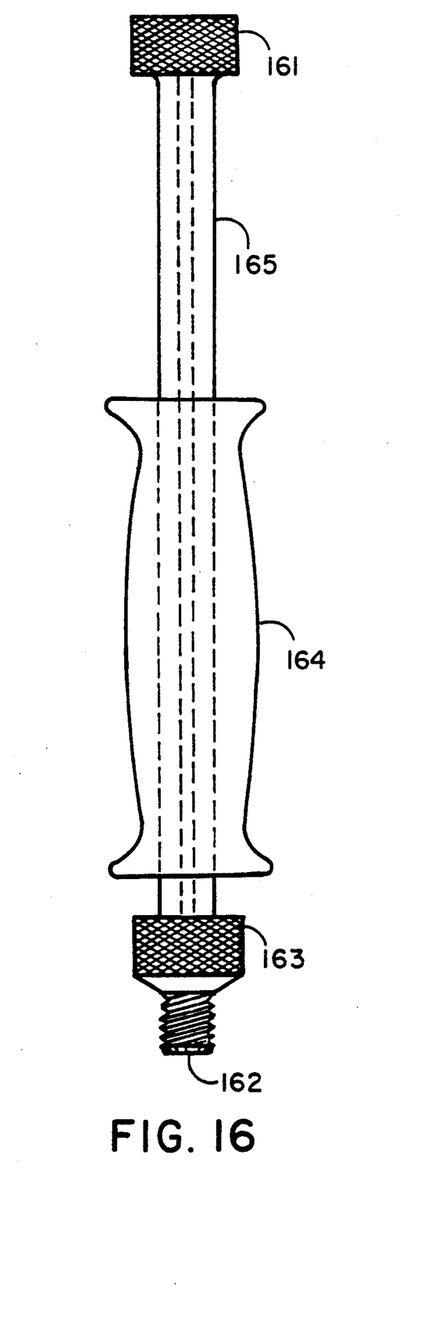
FIG. 16 is an elevation of a slap hammer in accordance with a preferred embodiment of the invention.

FIG. 16 illustrates a slap hammer for use in inserting the nail 31, including handle 161, insertion tip 162, and lower stop 163. The slapper 164 is slidably mounted on the rod 165 and travels between the handle 161 and lower stop 163.

What is claimed is:

1. A method, of locking an intramedullary nail, having a proximal end and a distal end, to a bone, the method comprising locking the distal portion of the bone, by the steps of:
- (A) inserting a guide wire into the medullary canal of the bone;
- (B) obtaining a locator that includes grab means for grabbing the guide wire;
- (C) inserting the locator through a pilot hole in the near cortex of the bone in a suitable distal location and causing the grab means to grab the guide wire; and
- (D) inserting an intramedullary nail along the guide wire into the medullary canal until it contacts the locator.

2. A method according to claim 1, the method further comprising, prior to step (D), the step of obtaining an intramedullary nail, having a proximal end and a distal end;

wherein the locator includes engagement means for engaging with the distal end of the intramedullary nail;

wherein the intramedullary nail is suitably configured at its distal end to engage with the engagement means on the locator; and wherein step (D) further includes inserting the intramedullary nail into the medullary canal until it engages with the engagement means of the locator.

3. A method according to claim 2, further comprising:
- (F) engaging a first region of a distal alignment fixture with the locator and using the distal alignment fixture for determining the location of a first distal locking hole.

4. A method according to claim 3, further comprising:
- (I) drilling the first distal locking hole in the location determined in step (F); and
- (J) using a suitable fixture mounted to a member inserted in the first distal locking hole for determining the location of a second distal locking hole.

5. A method according to claim 4, further comprising, immediately prior to step (F), the step of removing the guide wire from the intramedullary canal.

6. A method according to claim 1, further comprising:
- (E) engaging a first region of a distal alignment fixture with the locator and using the distal alignment fixture for determining the location of a first distal locking hole.

7. A method according to claim 6, further comprising:
- (G) drilling the first distal locking hole in the location determined in step (E); and
- (H) using a suitable fixture mounted to a member inserted in the first distal locking hole for determining the location of a second distal locking hole.

8. A method according to claim 6, further comprising, immediately prior to step (E), the step of removing the guide wire from the intramedullary canal.

9. An apparatus for fixation of a bone having a medullary canal, for use with a guide wire inserted into the medullary canal and an intramedullary nail, having proximal and distal ends, that has ben inserted along the guide wire into the medullary canal, the apparatus comprising:

a locator, for insertion into a pilot hole drilled transversely with respect to the axis of the medullary canal, the locator having (i) grab means for grabbing the guide wire and (ii) engagement means for engaging with the distal end of the intramedullary nail;

wherein the intramedullary nail is suitably configured at its distal end for engagement with the engagement means on the locator.

10. An apparatus according to claim 9, wherein the locator has a longitudinal axis and proximal and distal ends, the grab means is disposed at the distal end of the locator, and the engagement means includes an annular recess in the locator.

11. An apparatus according to claim 10, wherein the locator includes a sleeve, having a proximal end and a distal end, slidably mounted on the longitudinal axis of the locator, and the annular recess in the locator is formed in the distal end of the sleeve.

12. An apparatus according to claim 11, further comprising:

a distal alignment fixture engagable against the sleeve of the locator, the fixture including an alignment hole for locating a hole to be drilled in the bone.

13. An apparatus according to claim 9, further comprising:

a distal alignment fixture engagable against the locator, the fixture including an alignment hole for locating a hole to be drilled in the bone.

14. An apparatus for fixation of a bone having a medullary canal, for use with a guide wire inserted into the medullary canal and an intramedullary nail, having proximal and distal ends, that has been inserted along the guide wire into the medullary canal, the apparatus comprising:

a locator, for insertion into a pilot hole drilled transversely with respect to the axis of the medullary canal, the locator having (i) grab means for grabbing the guide wire and (ii) engagement means for engaging with the distal end of the intramedullary nail;

wherein the intramedullary nail is suitably configured at its distal end for engagement with the engagement means on the locator;

wherein the locator has a longitudinal axis and proximal and distal ends, the grab means is disposed at the distal end of the locator, and the engagement means includes an annular recess in the locator;

wherein the locator includes a sleeve, having a proximal end and a distal end, slidably mounted on the longitudinal axis of the locator, and the annular recess in the locator is formed in the distal end of the sleeve; and wherein the grab means includes a hook and the sleeve is formed in such a way as to substantially surround the hook when the sleeve is slid to its most distal location along the longitudinal axis of the locator.

15. An apparatus according to claim 14, wherein the sleeve includes a U-shaped receiving region for receiving the hook.

16. An intramedullary nail comprising:

a prolongated member having (i) a front and a rear, (ii) a wall forming an interior channel, (iii) a longitudinal axis in the channel, and (iv) a distal end thereof at which the wall has an end defining an opening in the front of the member, such opening lying generally in a plane that is obliquely disposed with respect to the longitudinal axis so as to enable a tip of a locator, such tip being disposed perpendicularly to the longitudinal axis, to enter the channel from the front of the member; and wherein the end of the wall is further shaped in such a manner that, to facilitate positioning of the member and to cause its rotation, to the extent necessary on encountering the locator thus disposed for engaging the location, the axial position of a projection of a location on the end of the wall onto the longitudinal axis, as a function of angular orientation of the location about the longitudinal axis, varies smoothly with bilateral symmetry from the most distal axial position, associated with an angular orientation at the rear of the member, to a pair of shorter axial positions associated with angular orientations of locations on the wall at points spaced apart by a distance approximately equal to the diameter of the locator's tip, at which points the wall is approximately parallel to the longitudinal axis; and wherein, in the angular orientations lying predominantly between such points, the wall defines a region into which the locator may be positively engaged.

* * * * *